(12) United States Patent
Yam et al.

(10) Patent No.: US 6,346,096 B1
(45) Date of Patent: Feb. 12, 2002

(54) MEDICAL DRAINAGE DEVICE WITH FLOW RESTRICTION FEATURE

(75) Inventors: Jacky Yam; Alan Ranford, both of St. Louis, MO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/521,491

(22) Filed: Mar. 9, 2000

Related U.S. Application Data (60) Provisional application No. 60/123,479, filed on Mar. 9, 1999.

(51) Int. Cl.⁷ ............................................... A61M 1/00
(52) U.S. Cl. ...................... 604/321; 604/4.01; 604/317; 604/319
(58) Field of Search ................................ 604/317, 321, 604/323, 324, 4.01, 6.15, 403; D24/108, 121; 137/205

(56) References Cited

U.S. PATENT DOCUMENTS

| | | |
|---|---|---|
| 3,646,935 A | 3/1972 | Holbrook et al. |
| 3,742,934 A | 7/1973 | Holbrook et al. |
| 3,937,213 A | 2/1976 | McDonald |
| 3,946,735 A | 3/1976 | DeWall |
| 3,989,046 A | 11/1976 | Pannier, Jr. et al. |
| 4,317,525 A | 3/1982 | Schuessier et al. |
| 4,455,140 A | 6/1984 | Joslin |
| 4,870,975 A | 10/1989 | Cronk et al. |
| 4,988,342 A | 1/1991 | Herweck et al. ............. 604/321 |
| 5,002,534 A | 3/1991 | Rosenblatt |
| 5,067,950 A | 11/1991 | Broadnax, Jr. |
| 5,078,704 A | 1/1992 | Wejnar |
| 5,234,403 A | 8/1993 | Yoda et al. |
| 5,437,836 A | 8/1995 | Yamada |
| 5,542,939 A | 8/1996 | Onodera et al. |
| 5,549,585 A | 8/1996 | Maher et al. |
| 5,584,825 A | 12/1996 | Smith |
| 5,620,428 A | 4/1997 | Hand |
| 5,683,371 A | 11/1997 | Hand |
| 5,688,255 A | 11/1997 | Hand |
| 5,871,476 A | 2/1999 | Hand |
| 5,944,703 A | 8/1999 | Dixon et al. |

Primary Examiner—Sharon Kennedy
Assistant Examiner—Catherine Serke
(74) Attorney, Agent, or Firm—Ari M. Bai; Greensfelder, Hemker & Gale, PC (57) ABSTRACT

The present invention provides for a dual port arrangement for a water seal chamber of a drainage device for channeling and restricting fluid flow through the water seal during normal operation of the device when the patient is breathing normally, while preventing the breach of the water seal during reverse flow conditions when the patient takes a sudden and deep inhalation. The dual port arrangement comprises a narrow side port and a low profile tunnel port defining an elongated conduit interposed between and in communication with both arms of the water seal chamber. The side port has a thin slot configuration that restricts fluid flow communication through the side port, and the back tunnel port defines a low profile, elongated conduit with openings that channel fluid flow between both arms of the water seal chamber. The elongated configuration of the conduit prevents a steep water gradient from falling below the upper portion of the conduit opening during reverse flow conditions.

25 Claims, 6 Drawing Sheets

MEDICAL DRAINAGE DEVICE WITH FLOW RESTRICTION FEATURE

This is a non-provisional application based on provisional application Ser. No. 60/123,479 filed Mar. 9, 1999.

BACKGROUND OF THE INVENTION

1. Field of the Invention

The present invention relates to a medical device for draining fluid from the body cavity of a patient, and particularly to a drainage apparatus having a water seal chamber that restricts and channels the passage of fluid. More specifically, the present invention relates to a dual port arrangement for a water seal chamber that prevents the breach of the water seal during reverse flow conditions inside the drainage device.

2. Prior Art

A drainage device is an apparatus for suctioning gases and liquids from the pleural cavity of patients. The pleural cavity lies within the rib cage above the diaphragm and is surrounded by the pleural membrane. The pleural cavity contains both lungs, which in their normal expanded state fill the pleural cavity. Several conditions and diseases such as interventional surgery, trauma, emphysema and various infections can cause a build up of liquid and gases around the lungs in the pleural cavity. When this occurs, it causes the lungs to collapse to a volume much less than that of the pleural cavity, thereby severely impairing the breathing functions of the patient. The lungs can be re-expanded to their normal state to fill the pleural cavity by draining the liquid and gases from the pleural cavity using a drainage device.

Drainage devices are also used during autotransfusion for recovering autologuous blood from the patient's pleural and mediastinal cavities and transfusing that blood back into the patient. Autotransfusion using recovered autologuous blood offers significant advantages over normal transfusion procedures which use homologous blood from other humans. Autologous blood reinfused back into the patient reduces the risk of adverse reactions by the patient and transmission of infectious disease while supplying a readily available source of compatible blood to the patient.

Various drainage devices have been developed to drain and collect fluid from the pleural cavity of a patient for subsequent reinfusion back into the patient. U.S. Pat. No. 4,857,042 to Schneider illustrates the prior art development of drainage devices. The Schneider device comprises a closed vessel which includes a collection chamber for the collection of fluid from the pleural cavity, a water seal chamber for preventing passage of gas from the atmosphere into the patient's pleural and mediastinal cavities, and a manometer chamber for regulating the degree of vacuum in the drainage device. The water seal chamber is a U-shaped chamber having two vertical arms that meet through a single port located at a bottom portion of the water seal chamber. A predetermined amount of water, called the water seal, is disposed along the bottom portion of the U-shaped chamber which functions as a one-way barrier that effectively separates one arm of the chamber from the other arm such that gas and atmospheric air are prevented from flowing into the collection chamber, while permitting gas to exit therefrom. The water seal chamber is configured so that the arm upstream of the water seal chamber communicates directly with the collection chamber of the drainage device and the downstream arm of the water seal chamber communicates either with a suction source when the drainage device is used in a vacuum drainage mode or atmosphere when the device is used in a gravity drainage mode. When the drainage device is used in the vacuum drainage mode, the health care practitioner applies a source of suction to the suction port which causes a low pressure area to be established between the water seal and the suction control chamber and a negative pressure range to be maintained inside the collection chamber. Maintaining a negative pressure range inside the collection chamber causes shed fluids to be evacuated from the pleural cavity of a patient and deposited inside the collection chamber. In the gravity drain mode, no vacuum is applied to the drainage device and only a small negative pressure generated by the patient's inhalations is present in the collection chamber. To drain the pleural cavity of fluid, the drainage device is located below the patient such that the force of gravity in combination with the small negative pressure in the collection chamber draws shed fluid from the patient and into the drainage device. A collection port is provided along the surface of the collection chamber for the entry of shed blood and gases drained from the patient's pleural cavity through a thoracotomy tube and deposited inside the collection chamber. The drainage device may also be connected to a blood compatible pump for pumping autologuous blood through an outlet port provided along the surface of the collection chamber for reinfusion back into the patient when the drainage device is used for autotransfusion.

The Schnieder device is also provided with a valve mechanism above the water seal chamber to permit the passage of fluid from the water seal chamber in the event of a sudden increase in negative pressure inside the collection chamber, such as when the patient deeply inhales during breathing exercises. Unfortunately, a rather deep and quick inhalation by the patient, or a manual stripping of the patient's thoracotomy tube by a health care practitioner running his or her hands along the tube in order to remove blood clots formed along the tube, may cause a sudden breach in the water seal which the valve mechanism of Schneider is not designed to prevent. A breach of the water seal occurs when negative pressure inside the collection chamber is abruptly increased by the aforementioned causes. This sudden increase in negative pressure inside the collection chamber causes reverse flow conditions inside the drainage device which produces a deep water gradient or plane that breaches the water seal and permits gases to rush from the downstream arm of the water seal chamber to the upstream arm. This reverse flow condition forces the level of the water seal at the downstream arm down below the upper portion of the water seal port and causes the breach the water seal. Reverse flow conditions occur whenever the negative pressure within the upstream arm becomes greater than the negative pressure in the downstream arm. This change in pressure causes the normal fluid flow from the upstream arm to downstream arm to reverse direction. When the water seal is breached during reverse flow conditions gases are permitted to freely flow through the water seal port above the water seal towards the upstream arm of the water seal chamber which communicates with the collection chamber. Such free flow of gases into the collection chamber is deemed undesirable since it lowers the generally constant negative pressure required to be maintained inside the collection chamber which communicates directly with the patent's pleural cavity. The sudden flow of gases through a breach in the water seal has a negative impact on the patient during convalescence because the lowering of the negative pressure range usually maintained in the collection chamber inhibits the patient from properly expanding his lungs. When the negative pressure maintained inside the collection chamber is decreased below this predetermined negative pressure range, it makes it more difficult for the patient to fully expand his lungs during inhalation exercises and unnecessarily lengthens the time of convalescence. Moreover, gases flowing into the collection chamber during reverse flow conditions may be visually undesirable to the patient because gas flow through the water seal during reverse flow conditions causes a migration of bubbles towards the upstream arm which can be seen through the transparent body of the closed vessel and may give the patient the incorrect perception that the drainage device is not operating correctly.

It has been found that the configuration of the single port arrangement used to separate the two arms of the water seal chamber in prior art drainage devices is insufficient to prevent breach of the water seal caused by reverse flow conditions during a sudden deep inhalation by the patient or manual stripping of the thoracatic tube by a health care practitioner. Therefore, there is a need in the art for a drainage device which includes an improved water seal port arrangement that substantially prevents the breach of the water seal during the reverse flow conditions.

OBJECTS AND SUMMARY OF THE INVENTION

In brief summary, the present invention overcomes and substantially alleviates the deficiencies in the prior art by providing a novel dual port arrangement for a water seal chamber adapted for substantially preventing the migration of gas bubbles through the water seal and the breach of the water seal in a medical drainage device during reverse flow conditions. The dual port arrangement according to the present invention comprises an upper side port and a lower tunnel port which both communicate with the upstream and downstream arms of the water seal chamber. The side port has a narrow slot configuration that extends along a portion of the water seal chamber side wall that separates the upstream and downstream arms. On the other hand, the tunnel port defines a low profile, elongated conduit that extends along the bottom portion and through the back wall of the water seal chamber.

The narrow slot configuration of the side port functions to restrict fluid flow communication through the side port and greatly inhibit the breach of the water seal during reverse flow conditions when incoming fluid flow into the collection chamber forces the water seal into a steep water gradient profile at the downstream arm and forces the level of the water seal to fall below the upper portion of the water chamber port found in the prior art device. The configuration of dual port arrangement of the present invention channels restricts fluid flow and fluid through two alternative ports in the water seal chamber which greatly inhibits the breach of the water seal during reverse flow conditions. Further, the elongated conduit defined by the tunnel port provides a sufficient conduit for the evacuation of fluid from the collection chamber during normal operation of the drainage device while being configured to substantially inhibit the deep water gradient of the water seal from falling below the upper portion of tunnel port and cause the breach the water seal during reverse flow conditions. This is accomplished by locating the elongated conduit of the tunnel port along the bottom portion of the water seal chamber with one end of the tunnel in communication with the downstream arm and the other end of the tunnel in communication with the upstream arm of the water seal chamber. The elongated conduit presents a low profile relative to the rest of the water seal chamber which greatly inhibits a steep water gradient from falling completely below the upper portion of the tunnel. It is this combination of a side port with a restricted flow rate and a tunnel port having a low profile, elongated configuration that provides a means for channeling fluid flow through the water seal chamber such that a deep water gradient is unable to cause a breach of the water seal during reverse flow conditions.

Accordingly, the primary object of the present invention is to provide a multi-port arrangement between two arms of a water seal chamber of a drainage device configured to prevent breach of the water seal during reverse flow conditions caused by an increase in negative pressure inside the collection chamber.

Another object of the present invention is to provide an elongated, low profile conduit for channeling fluid flow through the water seal chamber.

A further object of the present invention is to provide an elongated, low profile conduit which permits sufficient fluid flow through the port during normal operation of the drainage device while preventing the breach of the water seal during reverse flow conditions.

Another further object of the present invention is to provide a dual port arrangement for restricting the flow of fluid through the water seal chamber.

These and other objects of the present invention are realized in the preferred embodiment of the present invention, described by way of example and not by way of limitation, which provides for medical drainage device having a dual port arrangement that prevents breach of the water seal during reverse flow conditions.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
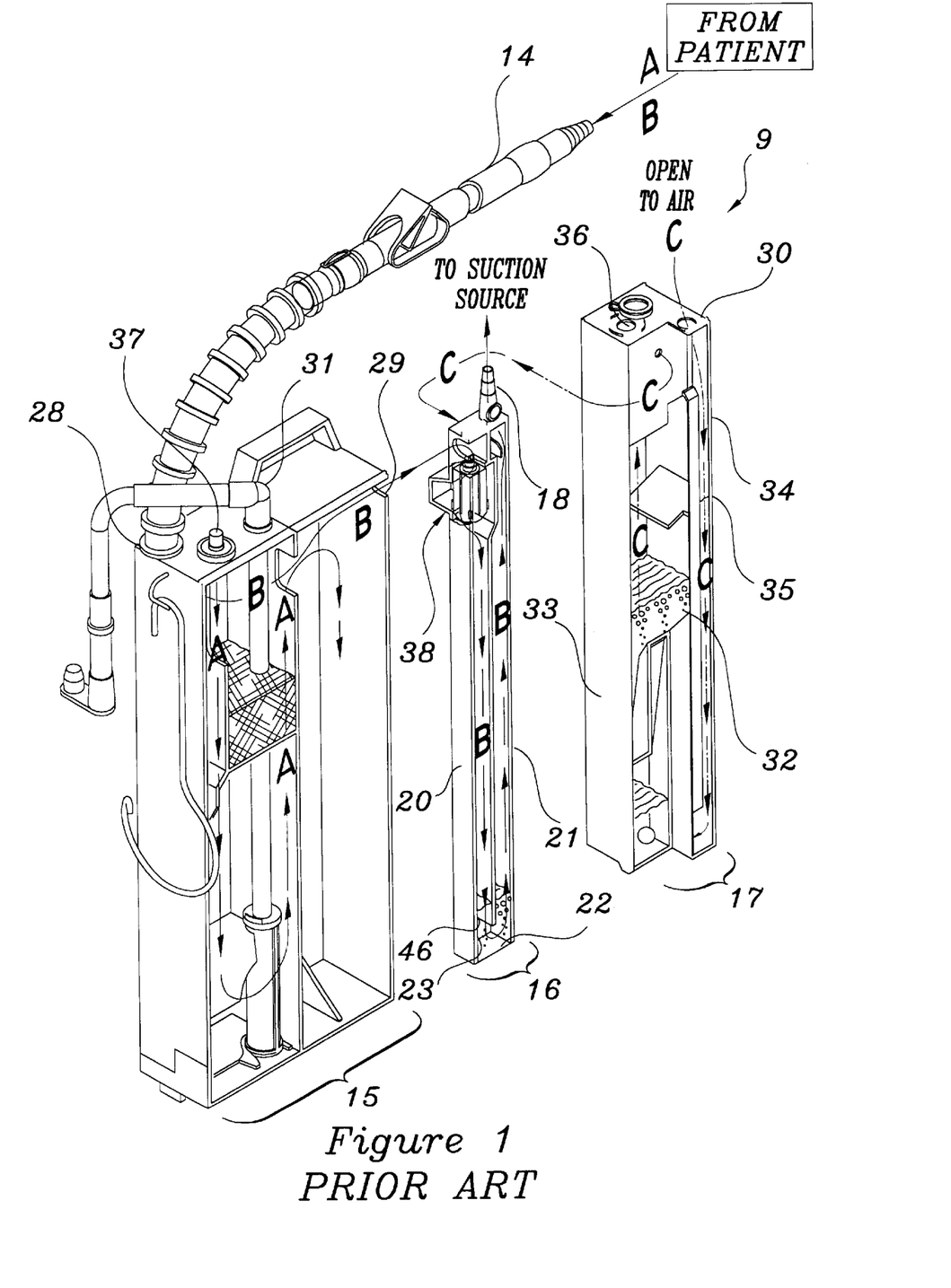
FIG. 1 is a partial cross section showing an exploded view of a prior art drainage device illustrating the basic operation thereof.
Figure 2A:
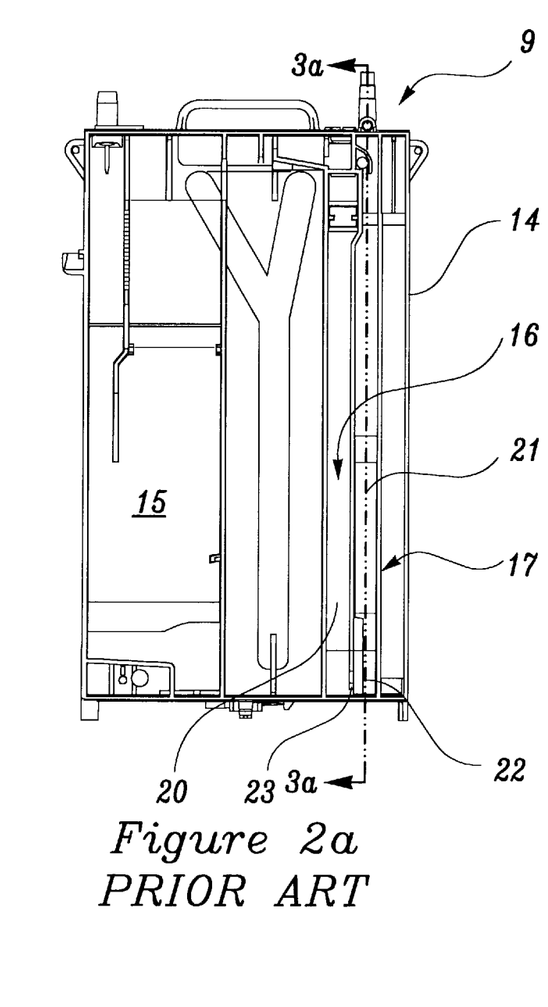
FIG. 2a is a front view of a drainage device showing a prior art water seal port arrangement.
Figure 2B:
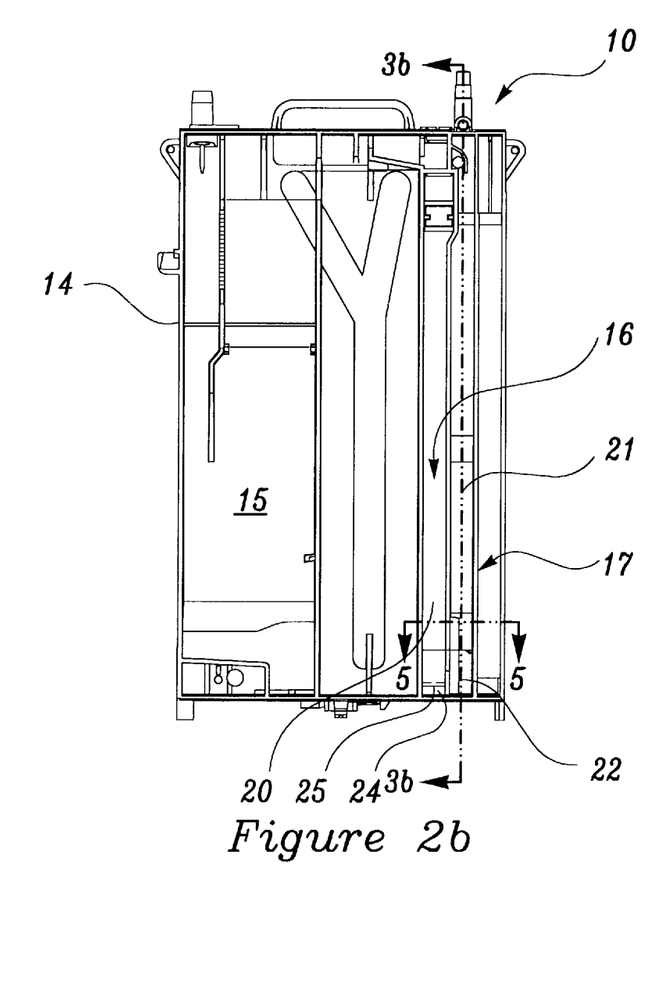
FIG. 2b is a front view of the drainage device showing the water seal chamber port arrangement according to the present invention.

Referring to the drawings, the preferred embodiment of the drainage device with flow restriction feature of the present invention is illustrated and generally indicated as 10 in FIG. 2b. Referring to FIG. 1, a prior art drainage device 9 is shown without the flow restriction feature according to the present invention for the purpose of illustrating the basic operation of a prior art medical drainage device. Drainage device 9 is connected to a patient (not shown) through a flexible, infusion tube 14 for use as a conduit to transfer and deposit shed fluid from the patient into drainage unit 9. Fluid flow A denotes the pathway of the fluid flow within drainage device 9 during normal operation.

The basic operation of drainage device 9 is disclosed in U.S. Pat. No. 4,798,578 to Ranford and is herein incorporated by reference in its entirety. In brief summary, the drainage device 9 operates to collect fluid drawn from a patient's pleural cavity through infusion tube 14 using suction generated by a source of negative pressure applied to the closed vessel of device 9. If desired, drainage device 9 may also be used as an autotransfusion system for the reinfusion of fluid back to the circulatory system of the patient.

The general process of the sterile collection of fluid inside the drainage device 9 drawn from the patient begins by drawing fluid from the patient's pleural cavity through infusion tube 14 attached to device 9 using either the vacuum drainage mode or gravity drainage mode. In the vacuum drainage mode, a suction source (not shown) is applied to drainage device 9 which provides a negative pressure thereon and creates a positive fluid flow A from the patient into device 9. The suction forces shed fluid from the patient through infusion tube 14 and into a collection chamber 15 of drainage device 9. In the gravity drainage mode, no suction source is applied to the drainage device 9. Rather, drainage device 9 is placed in a location below the patient and the force of gravity in combination with a small negative pressure present in the collection chamber 15 provide sufficient force to draw shed fluid through infusion tube 14 and into chamber 15.

Preferably, collected fluid is removed from collection chamber 15 using a drop tube or other suitable conduit or outlet to evacuate collected fluid from drainage device 9 during autotransfusion. In alternative embodiments, the egress of fluid from the collection chamber 15 can be from any suitable site along the surface thereof where infusion tube 14 may be attached for reinfusion of fluid back to the patient, or device 9 may be used simply as a collection site for fluid. Once the fluid exits the collection chamber 15, it may be reinfused back to the patient's circulatory system using methods well known in the art.

The operative features of drainage device 9 will now be discussed in greater detail. Drainage device 9 comprises a closed vessel having three intercommunicating chambers consisting of the collection chamber 15, a water seal chamber 16 and a suction control chamber 17. Collection chamber 15 is designed to receive fluid drained from the patient's pleural and mediastinal cavities, but it may also function as a filtration site to filter fluid of unwanted debris and contaminants entrained in the fluid prior to reinfusion back to the patient. The other two chambers, the water seal chamber 16 and suction control chamber 17, serve to control and regulate fluid flow inside collection chamber 15 as well as the degree of negative pressure maintained inside the drainage device 9. In particular, the suction control chamber 17 provides regulation of the negative pressure range required to be maintained inside collection chamber 15 in order to provide sufficient suction to draw shed fluid from the patient. The negative pressure range maintained inside drainage device 9 is controlled by a column of water 32 disposed in the suction control chamber 17 which insures a continuous level of suction inside the pleural cavity and also alleviates concerns over possible tissue invagination during high levels of negative pressure within the body cavity.

As further shown in FIG. 1, suction control chamber 17 consists of a U-shaped chamber having first and second arms 33, 34, respectively. If the drainage device 9 is operating in vacuum drainage mode, a column of water 32 fills the suction control chamber 17 and extends upwardly a distance through both arms 33, 34 such that negative pressure within device 9 is maintained at a specific negative pressure range. First arm 33 defines an elongated vertical column communicating with a downstream arm 21 of water seal chamber 16 and a suction source (not shown), while the second arm 34 defines a similarly configured vertical column with one end open to atmospheric air which maintains a zone of atmospheric pressure in the portion of arm 34 above a water line 35. As illustrated, air flow C denotes the atmospheric air flow pathway through suction control chamber 17. Air flow C shows atmospheric air being drawn in second arm 34 through an open port 30 and into first arm 33 where it exits arm 33 through a suction port 18 towards the suction source. The height of the column of water 32 interposed between the first arm 33 exposed to a suction source and the second arm 34 which is at atmospheric pressure determines the level of negative pressure range maintained inside the collection chamber 15 as well as the low pressure area between the downstream arm 21 and the suction control chamber 17. For example, a column of water 32 20 cm high at the column translates to a negative pressure no higher than −20 cm of water inside the low pressure area between the downstream arm 21 and the suction control chamber 17. Further, water column 32 having a height of 20 cm will also translate to a negative pressure of −18 cm of water inside the collection chamber 15 with the pressure differential of −2 cm of water being caused by the decrease in negative pressure across water seal 22. U.S. Pat. No. 4,439,190 to Protzmann et al. discloses a more detailed description of a typical suction control chamber 17 and its operation is herein incorporated by reference.

The water seal chamber 16 provide a water barrier that prevents reflux of evacuated gas and fluid back to the patient by preventing reentry of evacuated fluid into the collection chamber using an air sensitive, buoyant valve 38 in combination with water seal 22 disposed along at the bottom portion of chamber 16. As illustrated in FIG. 1, fluid flow B depicts the flow of fluid through drainage device 9 when applying a suction source to suction port 18 located at the top portion of downstream arm 21. By applying a suction source to suction port 18, a low pressure area is established between the water seal 22 and the column of water 32. Further, as noted above, collection chamber 15 is maintained at a desired negative pressure range slightly below that of the low pressure area due to the decrease in negative pressure across the water seal 22. Accordingly, during normal operation of drainage device 9 fluid is forced to flow from collection chamber 15 and suction control chamber 17 towards the suction port 18. The applied suction to drainage device 9 evacuates fluid from the patient's pleural cavity (not shown) along infusion tube 14 and into collection chamber 15 through a collection port 28. As illustrated by fluid flow B, collected fluid passes through an opening 29 and into the upstream arm 20 of water seal chamber 16. Once inside the water seal chamber 16, fluid in the form of trapped gases collected in collection chamber 15 migrates through the water seal 22. After passing water seal 22, fluid travels up downstream arm 21 where the gases exit out through suction port 18. Thus, the applied suction generates a positive flow pathway through drainage device 9 which evacuates accumulated gases out of collection chamber 15 and through water seal 22.

As further shown, upstream arm 20 of water seal chamber 16 is in fluid flow communication with downstream arm 21 at one end and the collection chamber 15 at the other end thereof, while the downstream arm 21 communicates with upstream arm 20 at one end and the suction control chamber 17 at the other end. Upstream and downstream arms 20, 21 communicate through a single side port 23 located at the bottom portion of the water seal chamber 16. Water seal 22 functions as a protective one-way valve that allows gases to escape from the collection chamber 15, but prevents contaminated atmospheric air and evacuated gases from entering the collection chamber 15. By interposing the water seal 22 as a barrier along the bottom portion of water seal chamber 16, a pressure differential is established between upstream and downstream arms 20, 21 such that gases are allowed to migrate and pass through the water seal 22, and along downstream arm 21, but are prevented from returning in a reflux action. The difference in surface area between the two arms 20, 21 causes this pressure differential which prevents the reflux action. The importance in preventing reflux or re-entry of gases back into collection chamber 15 is that under certain respiratory conditions such entry of gases can cause a sudden decrease in negative pressure in collection chamber 15. Such a sudden decrease in negative pressure in collection chamber 15 can interfere with the normal respiratory function of the patient's lungs because a decrease in negative pressure inside collection chamber 15 greatly inhibits the patient's ability to fully expand his lungs.

In addition to water seal 22, which prevents any reflux of gases back into the collection chamber 15, an air flow sensitive, buoyant valve 38 is provided at the top portion of water seal chamber 16 as a further safeguard. Drainage device 9 is designed so that gases can escape through an automatic positive pressure relief valve 36 when an overpressure condition occurs inside the patient's pleural cavity, e.g. when the patient coughs. The automatic positive relief valve 36 is positioned on the top portion of drainage device 9 and is in fluid flow communication with the suction control chamber 17. Similarly, the collection chamber 15 has a negative pressure relief valve 37 which manually vents excess negative pressure from chamber 15 and the patient's pleural cavity when manually actuated by medical personnel.

As discussed above, fluid flow C represents the flow of ambient or atmospheric air through the drainage device 9. Once atmospheric air has passed through open port 30, air travels a pathway through first and second arms 33, 34 of suction control chamber 16 where it normally exits through suction port 18. However, during reverse flow conditions the water seal 22 can be breached when a sufficiently high negative pressure is generated inside the collection chamber 15 such that the negative pressure at the upstream arm 20 is higher than the negative pressure on the downstream arm 21 which causes atmospheric air to be drawn through downstream arm 21 and force down water seal 22 into a steep water gradient below the upper portion of side port 23. For example, during reverse flow conditions, the low pressure area between the downstream arm 21 and suction control chamber 17 might be at a negative pressure of −20 cm of water, while the collection chamber is maintained at a higher negative pressure of −24 cm of water. This pressure differential causes the upstream arm 20 to be at a negative pressure which is higher than the negative pressure at the downstream arm 21 which forces the water seal 22 into a steep water gradient. This steepening of the water seal 22 gradient can cause a breach or passage through water seal 22 when the level of the water seal falls below the upper portion of port 23 which permits atmospheric air to enter collection chamber 15, as illustrated by fluid flow C.

Referring to FIGS. 2a and 2b, drainage device 10 according to the present invention is similar in construction and operation to prior art drainage device 9 with the exception that the single side port 23 is replaced with a novel dual port arrangement. The dual port arrangement of the present invention comprises a side port 24, shaped as a narrow slot to restrict fluid flow, and an elongated tunnel port 25 which provides an alternate conduit for channeling fluid flow through the water seal chamber 16.

Figure 3A:
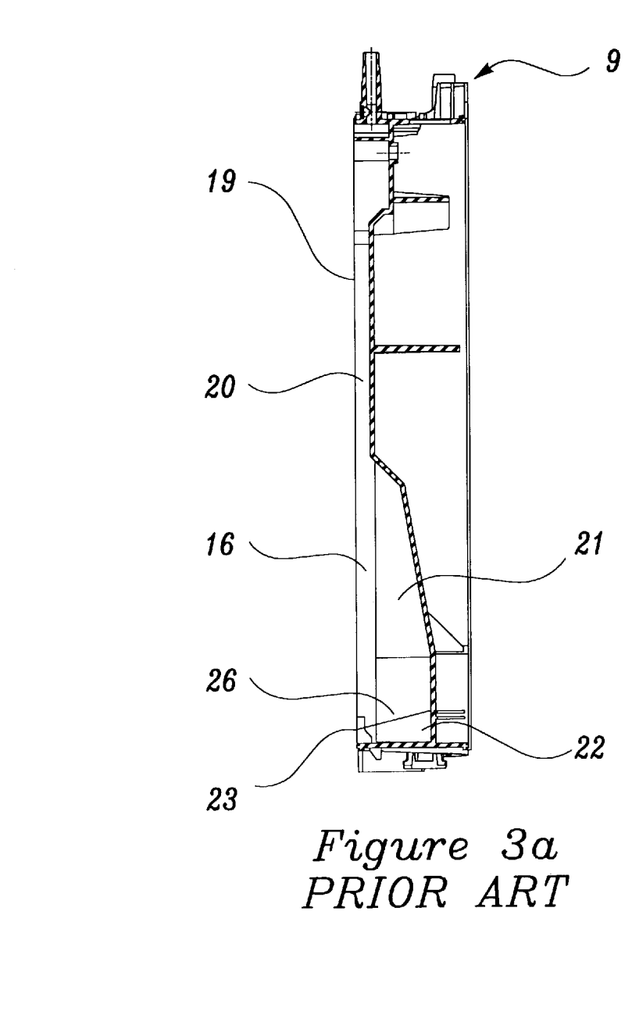
FIG. 3a is a cross sectional view of a prior art drainage device taken along line A—A shown in FIG. 2a illustrating the breach of the water seal.
Figure 3B:
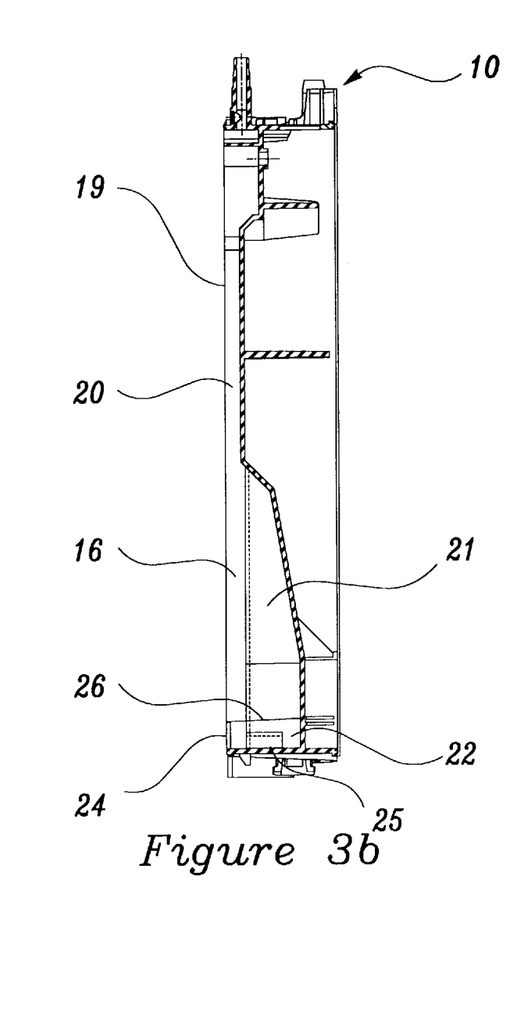
FIG. 3b is a cross sectional view of a drainage device taken along line B—B shown in FIG. 2b illustrating the operation of the dual port arrangement according to the present invention.
Figure 4:
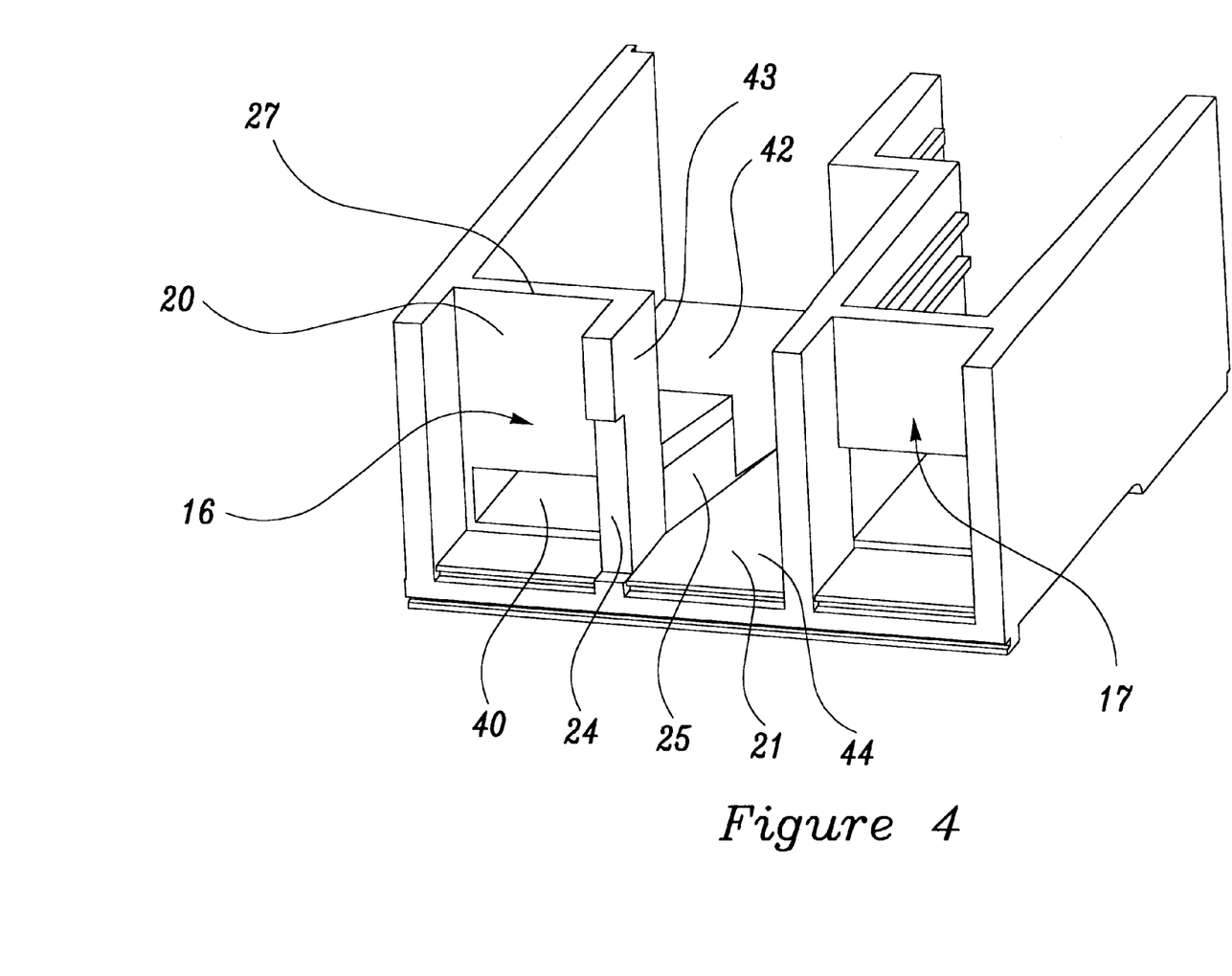
FIG. 4 is a fragmentary isometric view of the dual port arrangement according to the present invention.
Figure 5:
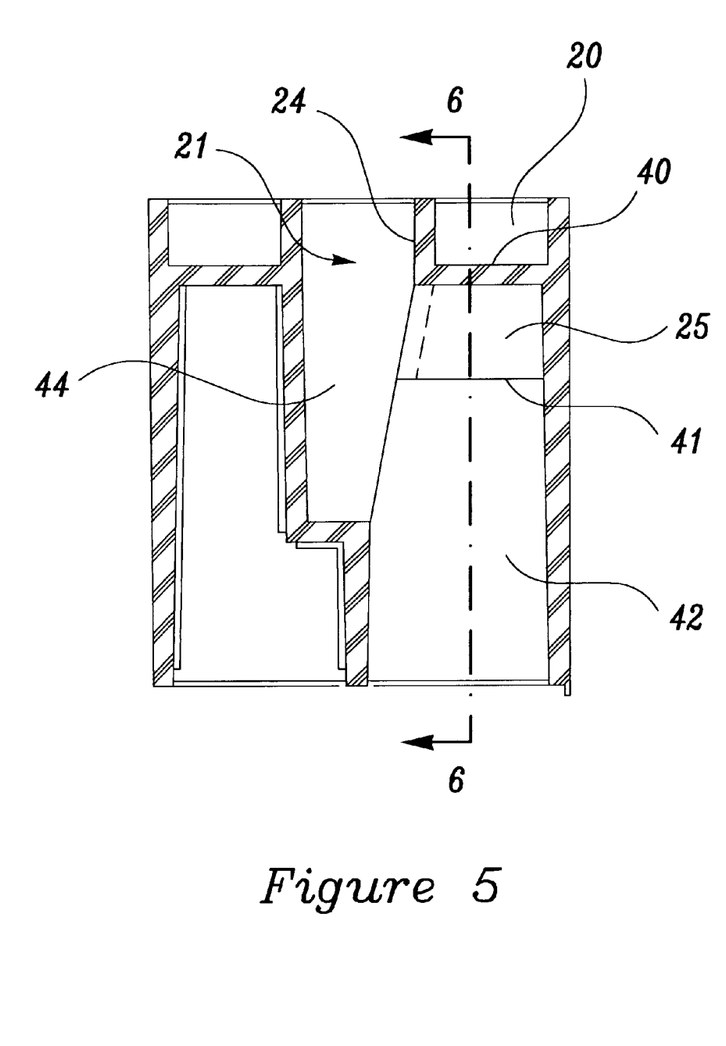
FIG. 5 is a cross sectional view of the dual port arrangement taken along line C—C shown in FIG. 2b according to the present invention.
Figure 6:
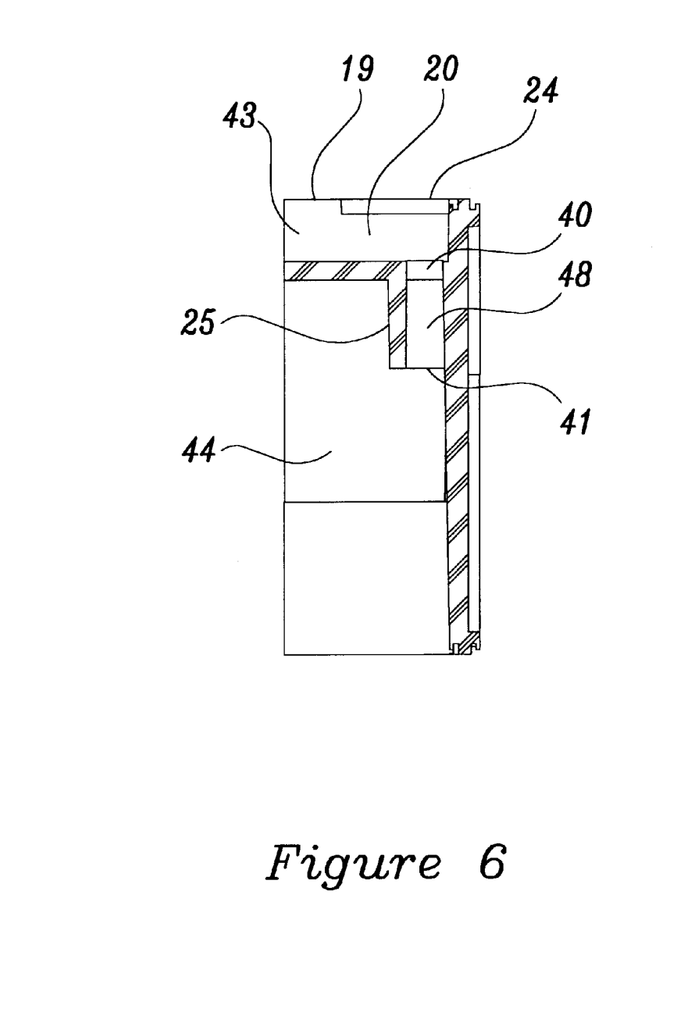
FIG. 6 is a cross sectional view of the dual port arrangement taken along line D—D shown in FIG. 5 according to the present invention.
Figure 7:
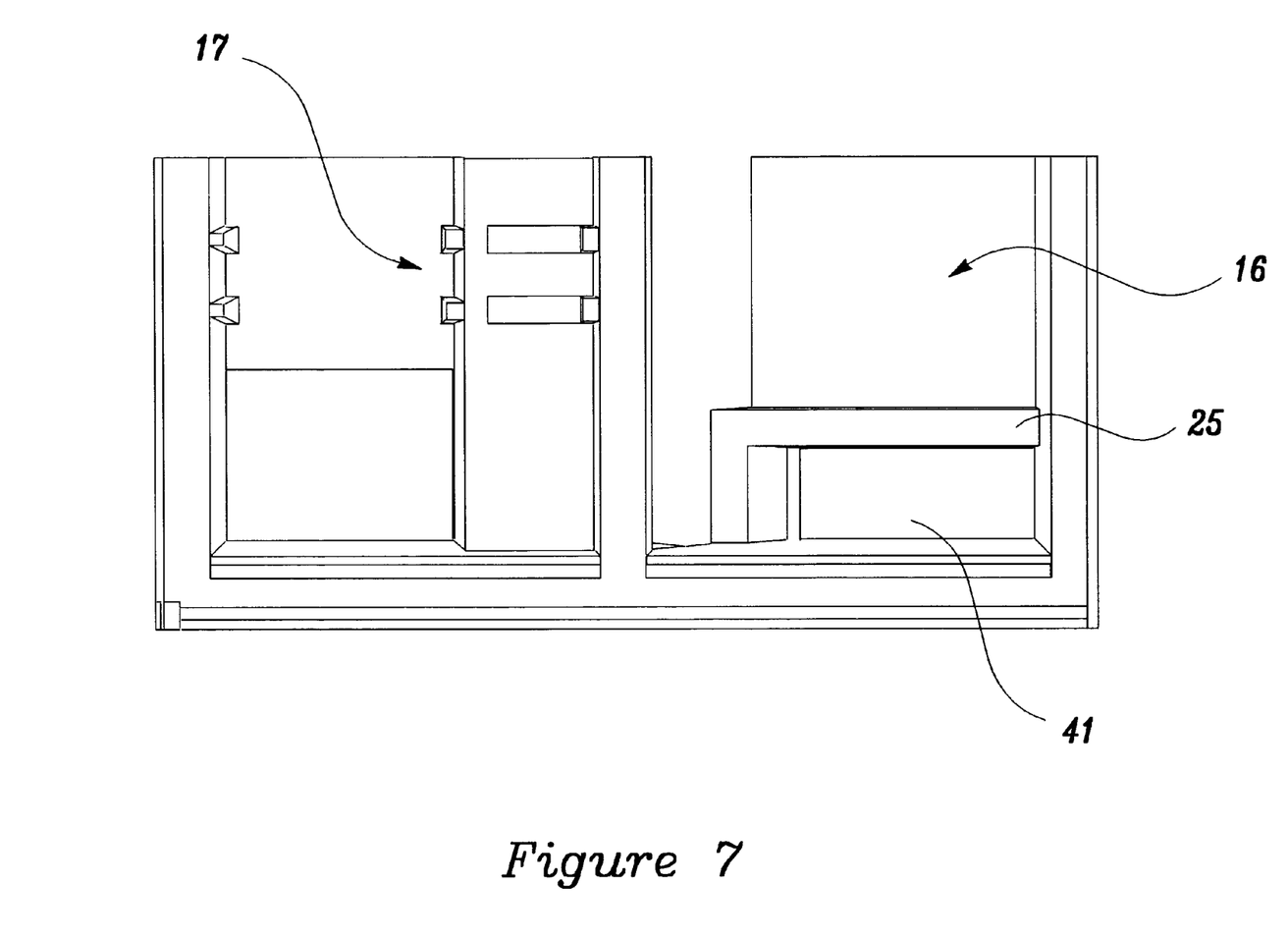
FIG. 7 is fragmentary back view of the dual port arrangement according to the present invention.

Referring to FIGS. 3a and 3b, cross sectional views comparing the operation of the prior art and present invention are illustrated. FIG. 3a shows the prior art drainage device 9 with the single side port 23 that permits passage of atmospheric air and gases through a breach in the water seal 22 caused by a steep water gradient 26 falling below the upper portion of port 23 during reverse flow conditions. In contrast, FIG. 3b shows the dual port arrangement of the present invention with the level of the water gradient 26 remaining above the upper portion of the side port 24 and tunnel port 25 during reverse flow conditions, thereby preventing any breach of water seal 22 as shall be discussed in greater detail below.

Referring to FIGS. 4–7, upstream arm 20 forms a generally rectangular cross section having a back wall 27 formed adjacent a side wall 43 that separates the upstream arm 20 from the downstream arm 21 of water seal chamber 16. The bottom portion of downstream arm 21 is divided into a lower back chamber 42 and a lower side chamber 44. The side port 24 is in communication between the upstream arm 20 and the lower side chamber 44, while the tunnel port 25 is in communication between the upstream arm 20 and the lower back chamber 42.

Tunnel port 25 defines a hollow, elongated conduit 48 which extends from back wall 27 to the lower back chamber 42 with elongated conduit 48 having a front opening 40 in communication with upstream arm 20 and a back opening 41 in communication with lower back chamber 42. The conduit 48 presents a substantially low profile relative to the side port 24 that prevents a steep water gradient in the downstream arm 21 caused by reverse flow conditions from falling below the upper portion of the conduit 48 and breach the water seal 22. As illustrated in FIG. 3b, tunnel port 25 is provided to channel fluid flow through water seal chamber 16 and insure sufficient fluid flow through openings 40, 41, during normal operation of drainage device 10. Conduit 48 prevents the breach of the water seal 22 that develops in downstream arm 21 during reverse flow conditions because a steep water gradient of water seal 22 has difficulty falling below the entire upper portion of conduit 48 due to its elongated configuration and allow air flow therethrough. In contrast to tunnel port 25, side port 24 has a narrow slot configuration formed between the side wall 43 and front panel 19 of drainage device 10 that extends vertically upward. The narrow slot shape of side port 24 is configured to restrict fluid flow between upstream and downstream arms 20, 21, during reverse flow conditions while permitting sufficient fluid flow during normal operation of drainage device 10.

Although the dual port arrangement of the present invention discloses a side port 24 with a single narrow slot configuration, any type of suitable port configuration which restricts fluid flow, for example an array of small slots, is felt to fall within the spirit and scope of the present invention. Further, in the alternative, tunnel port 25 may define any shape of elongated conduit 48, for example semi-circular, square, etc., which extends along the lower portion of the water seal chamber 16 and presents a relatively a low profile relative to side port 24 for channeling fluid flow through water seal chamber 16.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

What is claimed is:

1. A device for collection of fluids from a patient comprising:

a closed vessel, first, second and third intercommunicating chambers being defined by said closed vessel, said closed vessel further including first, second and third openings for communication with atmosphere, a vacuum source and a fluid collection tube connected to a patient, respectively, and a water seal and a water column disposed inside said third chamber and said second chamber, respectively, to define during normal operation of the system a first pressure differential and a second pressure differential for establishing fluid flow from said first and third openings through said second opening while maintaining a desired sub atmospheric pressure range inside said first chamber, said second opening being in direct communication with a low pressure side of said water column and said water seal, said second chamber including first and second arms which communicate with one another through a first port and a second port, wherein said first and second ports are configured such that the integrity of said water seal is maintained during reverse flow conditions inside said device.

2. The device according to claim 1, wherein said second port defines an elongated conduit for fluid flow therethrough.

3. The device according to claim 2, wherein said elongated conduit extends between said first arm and said second arm.

4. The device according to claim 1, wherein said second port is positioned lower relative to said first port.

5. The device according to claim 1, wherein said first port defines a narrow slot for fluid flow therethrough.

6. The device according to claim 1, wherein said reverse flow conditions occur when the patient generates a high negative pressure inside said closed vessel.

7. The device according to claim 6, wherein said high negative pressure is generated inside said first chamber.

8. The device according to claim 1, wherein during said reverse flow conditions unidirectional flow from said third chamber to said second chamber is established through said device.

9. A system for collection of fluids from a patient comprising:

a closed vessel, first, second and third intercommunicating chambers being defined by said closed vessel, said closed vessel further including first, second and third openings for communication with atmosphere, a vacuum source and a fluid collection tube connected to a patient, respectively, and a water seal and a water column disposed inside said third chamber and said second chamber, respectively, to define during normal operation of the system a first pressure differential and a second pressure differential for establishing a normal flow condition from said first and third openings to said second opening while maintaining a desired sub atmospheric pressure range inside said first chamber, said second opening being in direct communication with a low pressure side of said water column and said water seal, said second chamber including first and second arms which communicate with one another through a plurality of ports, wherein said plurality of ports are configured such that the integrity of said water seal is maintained when unidirectional flow is established from said second chamber to said first chamber.

10. The system according to claim 9, wherein said unidirectional flow from said first chamber to said first chamber is caused by a patient generating a sudden negative pressure within said closed vessel.

11. The system according to claim 9, wherein at least one of said plurality of ports has a slot configuration.

12. The system according to claim 9, wherein at least one of said plurality of ports defining an elongated conduit between said first and second arms, said elongated conduit having an upper surface interposed between opposed openings with one of said openings in communication with said first arm and another one of said plurality of ports in communication with said second arm.

13. The system according to claim 12, wherein said elongated conduit maintains the integrity of said water seal by preventing the level of said water seal from falling below said upper surface of said elongated conduit during.

14. A system for preventing the breach of a water seal inside a water seal chamber of a drainage device comprising:

a closed vessel, first, second and third intercommunicating chambers being defined by said closed vessel, said closed vessel further including first, second and third openings for communication with atmosphere, a vacuum source and a fluid collection tube connected to a patient, respectively, and a water seal and a water column disposed inside said third chamber and said second chamber, respectively, to define during normal operation of the system a first pressure differential generated between said first opening and said water column and a second pressure differential generated between said water column and said water seal, said first and second pressure differentials establishing a normal flow condition from said first and third openings to said second opening while maintaining a desired sub atmospheric pressure range inside said first chamber, said second opening being in direct communication with a low pressure side of said water column and said water seal, said second chamber including first and second arms which communicate with one another through a first port and a second port, said first port providing a pathway for restricting fluid flow between said first and second arms, said second port defining an elongated conduit for providing a pathway for channeling fluid flow of said second chamber between said first and second arms, wherein said first and second ports maintain the integrity of said water seal by restricting and channeling fluid flow, respectively, through said second chamber during reverse flow conditions.

15. The system according to claim 14, wherein said first and second ports maintain the integrity of said water seal by restricting air flow through said water seal during said reverse flow conditions.

16. The method of restricting fluid flow through a water seal chamber of a drainage device having a closed vessel which defines first, second and third intercommunicating chambers, the closed vessel further including first, second and third openings for communication with atmosphere, a vacuum source and a fluid collection tube connected to a patient, respectively, a water column and a water seal disposed inside the third chamber and the second chamber, respectively, to define during normal operation of the system a first pressure differential generated between the first opening and the water column and a second pressure differential generated between the water column and the water seal, the first and second pressure differentials establishing a normal flow condition from the first and third openings to the second opening while maintaining a desired sub atmospheric pressure range inside the first chamber, the second opening being in direct communication with a low pressure side of the water column and the water seal, the second chamber including first and second arms which communicate with one another through a first port and a second port, comprising the steps of:

a) establishing a high negative pressure inside the first chamber;

b) establishing reverse flow conditions through the water seal;

c) providing a fluid pathway through each of the first and second ports; and d) restricting fluid flow through each of the first and second ports.

17. The method according to claim 16, wherein said step of applying a high negative pressure further includes applying the high negative pressure through the fluid collection tube by a patient.

18. The method according to claim 16, wherein said step of applying the high negative pressure to the inside of the first chamber establishes a unidirectional fluid flow from the second chamber into the third chamber.

19. The method according to claim 17, wherein establishing unidirectional fluid flow from the second chamber into the first chamber increase the sub atmospheric pressure inside the first chamber.

20. The method according to claim 16, wherein said step c) further includes providing the fluid pathway through an elongated conduit.

21. The method according to claim 16, wherein during said reverse flow conditions the negative pressure inside the upstream arm is greater than the negative pressure inside the downstream arm.

22. A device for collection of fluids from a patient comprising:

a closed vessel, first, second and third intercommunicating chambers being defined by said closed vessel, said closed vessel further including first and second openings for communication with atmosphere and a fluid collection tube connected to a patient, respectively, a water seal disposed inside said second chamber to define during normal operation of the device a pressure differential between said first chamber and said third chamber for establishing fluid flow from said first opening to said atmosphere, said second chamber including upstream and downstream arms which communicate with one another through a plurality of ports, wherein said plurality of ports are configured such that the integrity of said water seal is maintained during reverse flow conditions inside said device.

23. The device according to claim 22, wherein during reverse flow conditions the negative pressure inside said downstream arm is greater than the negative pressure inside said upstream arm.

24. The device according to claim 22, wherein one of said plurality of ports has an elongated configuration and another one of said plurality of ports has a narrow configuration.

25. The device according to claim 22, wherein one of said plurality of ports restricts fluid flow through said second chamber and the another one of said plurality of ports channels fluid flow through said second chamber.

* * * * *